United States Patent [19]
Vonier et al.

[11] Patent Number: 5,478,193
[45] Date of Patent: Dec. 26, 1995

[54] CONDOM HANDLING AND ORIENTATION APPARATUS

[75] Inventors: Nathan Vonier, Hermitage, Tenn.; Jim Whitten, Albany, Ga.

[73] Assignee: Agri Dynamics, Inc., Albany, Ga.

[21] Appl. No.: 334,417

[22] Filed: Nov. 4, 1994

[51] Int. Cl.$^6$ .................................................. B65G 51/02
[52] U.S. Cl. ........................... 414/755; 198/396; 406/153
[58] Field of Search .............................. 406/86, 87, 191, 406/194, 151, 153; 209/905, 906; 414/755; 198/380, 396

[56] References Cited

U.S. PATENT DOCUMENTS

Re. 30,410  10/1980  Povlacs ................................. 406/87

Primary Examiner—Michael S. Huppert
Assistant Examiner—Janice L. Krizek
Attorney, Agent, or Firm—Thomas C. Saitta

[57] ABSTRACT

An apparatus for orienting and delivering individual condoms is disclosed comprising in general an orienting tube having an inner diameter sized slightly smaller than the outer diameter of the condom ring, whereby a suction is used to draw the non-oriented, randomly configured condom into, through and out of the tube. Each condom is oriented in the same orientation and configuration upon exiting the orientation tube, with the tip proceeding the main body of the condom, followed by the ring and open end. The invention further comprises a retrieving mechanism to pick up individual, non-oriented condoms and deliver the condoms to the orienting tube.

23 Claims, 2 Drawing Sheets

CONDOM HANDLING AND ORIENTATION APPARATUS

BACKGROUND OF THE INVENTION

This invention relates generally to an apparatus for orienting and delivering condoms adapted for use in combination with other apparatus which require delivery of successive condoms all oriented in the same manner and configuration for testing or other purposes. In particular, the invention relates to such devices which utilize suction means to orient and deliver the condoms.

Individual condoms must be tested prior to packaging and sale to determine whether the condom is free of minute holes. Typically, this is done by hand loading each condom onto a properly shaped metal mandrel and exposing the condom to an electrical field. Current will pass through any hole in the condom, thereby indicating that the condom is defective and should be rejected. The hand loading of condoms is very slow. There are currently no known apparatus for automatic loading of the condoms onto the mandrels, since until this invention no one has solved the problem of being able to rapidly orient and deliver a large number of condoms.

An object of the invention is to provide an apparatus which is able to successively deliver a large number of condoms which have been properly oriented for placement onto the testing mandrels. A further object is to provide such an apparatus which is capable of properly orienting the condoms no matter the configuration or orientation with which the condoms are presented to the apparatus. It is a further object to provide such an apparatus which utilizes suction means to orient and deliver the condoms.

SUMMARY OF THE INVENTION

The apparatus comprises in general retrieving means to present condoms into the orienting means, orienting means to orient each condom into the same configuration and orientation, receiving means to receive the oriented condom for further manipulation and suction means to move and orient the condoms. The retrieving means can be as simple as an opening to receive condoms inserted by hand, but preferably comprises an apparatus for picking individual condoms from a large receptacle and presenting each condom to the orienting means.

The suction means can comprise any type of device capable of creating a pressure differential such that air and objects are drawn through the orienting means and into the receiving means. The receiving means may comprise an apertured receptacle or nozzle, where the suction means draws air through the apertures to pull the condom through the orienting means and into the receiving means. The orienting means comprises a long circular tube, the inner diameter of the tube being sized slightly smaller than the outer diameter of the ring on the condom, such that contact between the ring and the inner wall of the orienting tube slows the ring as it is pulled through the tube. Because the ring of the condom acts as an anchor, the nipple or tip end of the condom will be drawn forward by the suction means, thereby orienting each condom into the same configuration.

Preferably, the retrieving means is a mechanical device which is capable of delivering individual condoms to the orienting tube, and may comprise an individual retrieval tube which is reciprocated into a large receptacle containing a number of non-oriented condoms. A suction is drawn through a small opening in the retrieval tube, enabling the retrieval tube to retrieve one condom only. As the retrieval tube reciprocates, the condom is positioned adjacent the orienting tube, where the suction means pulls the condom from the retrieval tube and into the orienting tube for delivery to the receiving means. In practice, a number of orienting tubes, with a corresponding number of retrieving means and receiving means, will be incorporated into a single condom testing or manipulating apparatus.

DETAILED DESCRIPTION OF THE INVENTION

Figure 1:
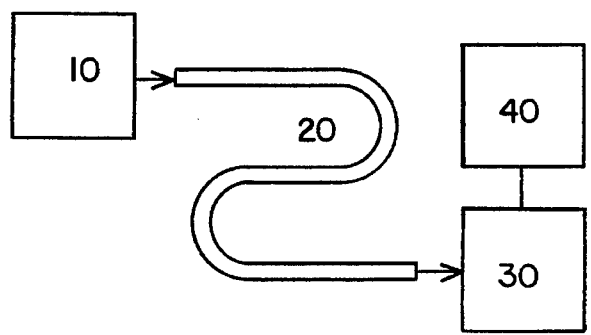
FIG. 1 is a stylized schematic showing the general components of the apparatus.

With reference now to the drawings, the invention will be described in terms of the best mode and preferred embodiment. The invention is an apparatus for the orientation and delivery of condoms in a repetitive and identical manner to a particular position or manipulator device, each condom being oriented and configured the same, such that further operations can be performed on each condom. Condoms are thin-walled, tubular objects made of latex or similar elastic material and comprise a nipple or tip end 71, a body 72 and a ring 73 formed by rolling up the condom at the open end 74. As shown in FIG. 1, the invention comprises generally retrieving means 10, orientation means 20, receiving means 30 and suction means 40. Retrieving means 10 comprises a mechanism to present or insert a single condom into orientation means 20, and for terms of this disclosure can consist of hand feeding the individual condoms. Suction means 40 is any suitable device known in the art capable of producing sufficient pressure differential to draw air and condoms through orientation means 20. For example, suction means 40 may comprise a blower or vacuum pump appropriately connected by conduits or a manifold device to create a suction draw in one or more orientation means 20.

Orientation means 20 in the preferred embodiment comprises a long tube 21 having an inner wall 22 with inner diameter 23. The tube 21 is impermeable to air and can be flexible or rigid. It is preferred that tube 21 have a number of curved or coiled portions rather than being strictly linear. The inner wall 22 is preferably smooth. Tube 21 has an inlet opening 24 for receiving the non-oriented condoms and an outlet opening 25 for dispensing the condoms to the receiving means 30. Air is drawn into inlet 24 and out of outlet 24 by suction means 40. The exact inner diameter 23 of tube 21 is a function of the size of the ring 73 of the particular condoms being oriented, and for typical condoms is preferably sized between one and one and a half inches, with the preferred inner diameter 23 being approximately one and one quarter inches. It is preferable that tube 21 be relatively long to insure that the condoms have sufficient time and distance to properly orient, and a total length between 35 and 100 feet is suitable, with a length of approximately 75 feet being preferred.

Figure 6:
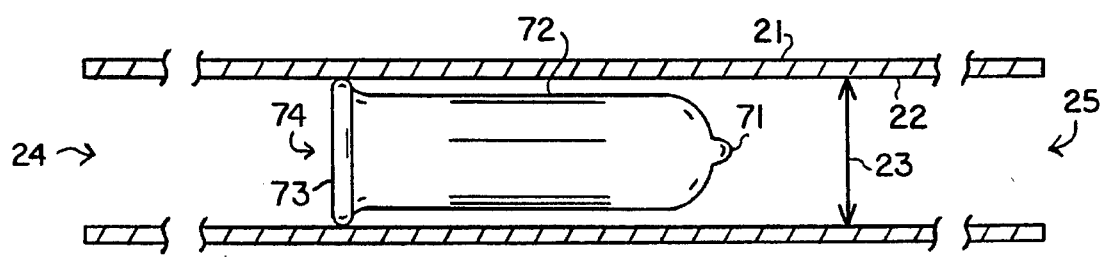
FIG. 6 is a cross-sectional view of a condom as oriented inside the orienting tube.

Orientation means 20 accomplishes the task of orienting a non-oriented, non-configured condom introduced into inlet opening 24 because the inner diameter 23 of inner wall 22 is sized to be slightly smaller than the outer diameter of condom ring 73. When inserted in inlet opening 24, the condom may be folded, twisted and positioned in any random orientation and configuration. As seen in FIG. 6, as the condom is drawn towards outlet opening 25 by suction means 40, the inner wall 22 compresses flexible ring 73. The friction between the ring 73 and the inner wall 22 creates a drag on the ring 73 but does not affect the main body 72 and tip 71 of the condom. The friction is not so great as to stop progress of the condom through tube 21, it only acts to slow it down. No matter the entry orientation and configuration of the condom, over the length of the orienting tube 21 the drag on the ring 73 results in the tip 71 being pulled to the front, i.e., in the direction of travel, by suction means 40. The curved or coiled portions of tube 21 increase the orientation efficiency, possibly because the different radial distances of the walls within each curved portion enable greater alignment of twisted sections of the condom. Every condom thus exits outlet opening 25 with the tip 71 in front, followed by the untwisted main body 72 and then ring 73.

Figure 4:
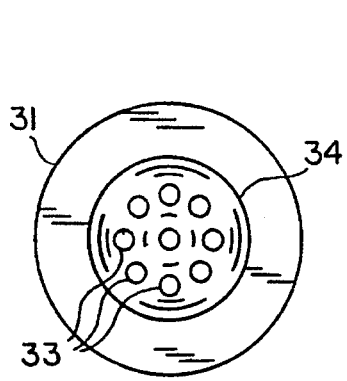
FIG. 4 is an end view of the nozzle receptacle.
Figure 5:
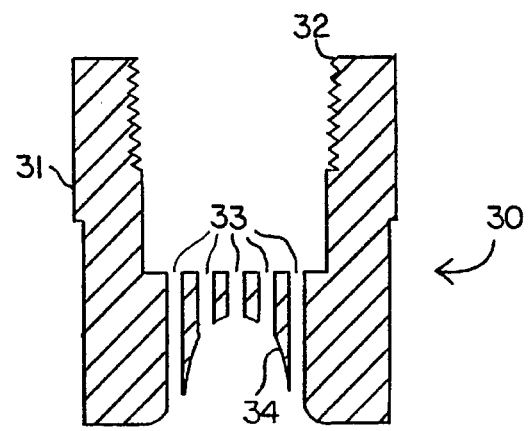
FIG. 5 is a cross-sectional view of the nozzle receptacle.

The apparatus is adapted to present each condom in the same orientation and configuration to the receiving means 30, which can be any device adapted to retain the condom in the correct position. In the embodiment shown in FIGS. 4 and 5, the receiving means 30 comprises receptacle nozzle 31, which is connected to conduit means of suction means 40 via threaded fitting 32. Nozzle 31 has a number of apertures 33 positioned generally symmetrically within a cup shaped wall 34, and suction means 40 draws air through these apertures 33. As the condom exits outlet opening 25 of orienting tube 21, the tip 71 is drawn to apertures 33 and into the cup portion 34 of nozzle 31, where it is held in place until the suction is released. Nozzle 31 can then be removed from orientation tube 21 to deposit the condom where required for further manipulation or testing, or tube 21 can be moved from nozzle 31, or a gated multiple outlet housing can be used such that movement of neither tube 21 or nozzle 31 is necessary to deliver the condom. Preferably nozzle 31 is vertically oriented such that the condom hangs downward with the tip 71 at the top and the open end 74 on the bottom.

Figure 2:
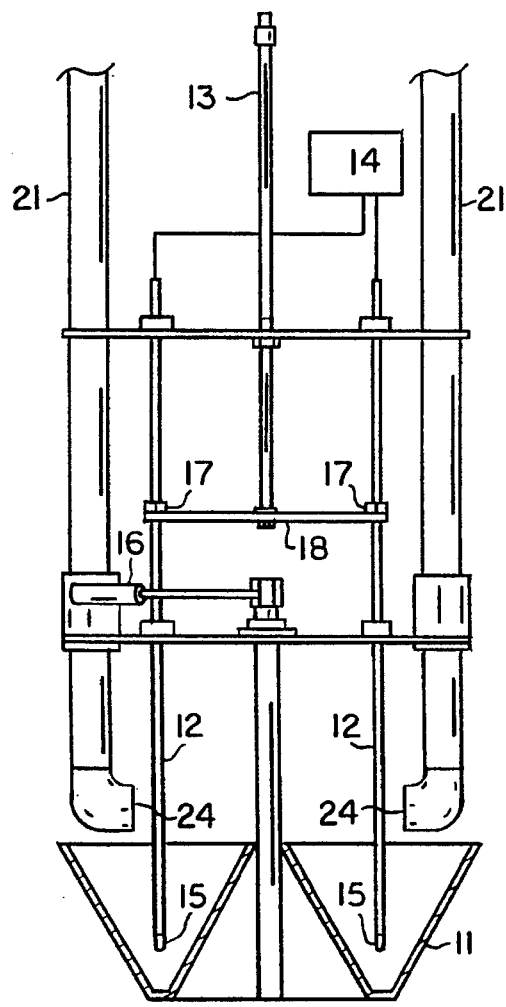
FIG. 2 is a view of the retrieving means and orienting means, with the retrieving means shown in the capture position.
Figure 3:
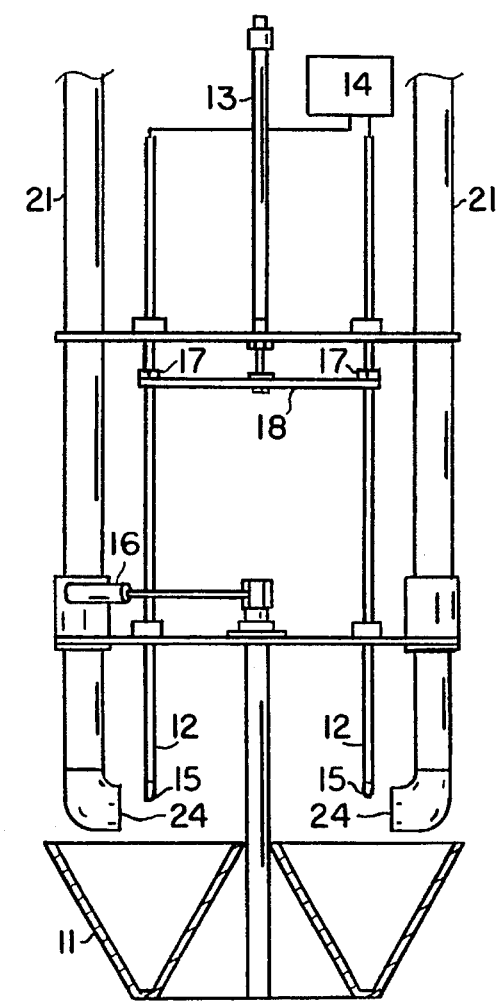
FIG. 3 is a view of the retrieving means and orienting means, with the retrieving means shown in the presentation position.

Because the apparatus is designed to greatly increase the speed with which condoms can be oriented and positioned, it is preferable that retrieving means 10 comprise a mechanical system for successively retrieving individual condoms from a receptacle containing a large number of non-oriented, randomly configured condoms and delivering each individual condom to the orientation means 20. A preferred embodiment for retrieving means 10 adapted for use with plural orientation means 20 is shown in FIGS. 2 and 3. Condom receptacle 11 is constructed to receive and hold a large number of condoms. It is preferred that the receptacle 11 be configured such that as condoms are removed by the retrieval tubes 12, more condoms will be positioned at the correct location for retrieval during the next cycle. An inverted cone shape preferably vibrated by receptacle movement means 16 will accomplish this, or in the preferred embodiment as shown a circular trough having a dual cone-shaped cross-section which is rotated by receptacle movement means 16 adequately positions condoms for successive retrieval by the reciprocating retrieval tubes 12. The vibration or rotation of receptacle 11 compensates for the packing action of the retrieval tubes 12 as they reciprocate vertically. Retrieval tubes comprise small tubes having an apertured tip 15, through which is drawn a small suction by retrieval suction means 14, shown here schematically. Retrieval suction means 14 can be any suitable device known for creating a pressure differential sufficient to retain a condom against the apertured tip 15 as it is drawn upward.

The operation of retrieving means 10 is illustrated by comparison of FIG. 2 with FIG. 3. FIG. 2 illustrates the capture or selection position. The retrieval tubes 12 are dropped into the receptacle 11 by reciprocating means 13, which can comprise an air cylinder or any other suitable mechanical configuration for vertically moving the retrieval tubes 12. The retrieval tubes 12 are preferably not fixed to reciprocating means 13, but instead have free travel in the upward direction. This is accomplished by the provision of a collar 17 attached to the retrieval tube 12. As the reciprocating means 13 is lowered and the apertured tip 15 contacts the top of the condom pile, the retrieval tube 12 remains stationary while the lower plate 18 moves to its extreme downward position. As the lower plate 18 is brought upward by reciprocating means 13, it contacts collar 17 and raises the apertured tip 15 and captured condom to the proper height adjacent the inlet opening 24 of the orienting tube 21, as shown in FIG. 3. The greater suction from suction means 40 strips the condom from the apertured tip 15 of retrieval tube 12, pulling it through the orienting tube 21 as previously described. The empty retrieval tube 12 is then lowered into the receptacle 11 to retrieve another condom, and this cycle is repeated.

It is understood that equivalents and substitutions to the elements and components set forth above may be obvious to those skilled in the art. The true scope and definition of the invention therefore is to be as set forth in the following claims.

We claim:

1. An apparatus for orienting and delivering condoms, said condoms having a tip and an open end bounded by a ring, said apparatus comprising:

(A) orienting means comprising a long orienting tube having an inlet opening for receiving condoms and an outlet opening for delivering said condoms oriented with the tip first and followed by the ring and open end;

(B) suction means to draw said condoms through said orienting means.

2. The apparatus of claim 1, further comprising retrieving means to introduce said condoms into said inlet opening.

3. The apparatus of claim 1, further comprising receiving means to receive said condoms from said outlet opening.

4. The apparatus of claim 3, wherein said suction means further draws said condoms to said receiving means.

5. The apparatus of claim 4, wherein said receiving means comprises an apertured nozzle adapted to receive said tip of said condoms and wherein said suction means draws through said apertured nozzle.

6. The apparatus of claim 1, wherein said orienting tube has an inner diameter smaller than the outer diameter of said ring of said condoms.

7. The apparatus of claim 6, wherein said inner diameter is between one and one and a half inches.

8. The apparatus of claim 7, wherein said inner diameter is approximately one and one quarter inches.

9. The apparatus of claim 1, wherein said orienting tube is between 35 and 100 feet in length.

10. The apparatus of claim 9, wherein said orienting tube is approximately 75 feet in length.

11. The apparatus of claim 2, wherein said retrieving means comprises one or more retrieval tubes, a receptacle to contain said condoms, reciprocating means to reciprocate said retrieval tubes into and out of said receptacle, and retrieval suction means connected to said retrieval tubes to hold said condoms, whereby said reciprocating means positions said condoms held by said retrieval tubes adjacent to said inlet opening of said orienting tube such that said suction means removes said condoms from said retrieval tubes.

12. The apparatus of claim 11, further comprising receptacle moving means for rotating or vibrating said receptacle.

13. An apparatus for orienting and delivering condoms, said condoms having a tip and an open end bounded by a ring, said apparatus comprising:

(A) orienting means comprising a long unobstructed orienting tube having an inlet opening for receiving condoms and an outlet opening for delivering said condoms oriented with the tip first and followed by the ring and open end, said orienting tube having an inner diameter smaller than the outer diameter of said ring of said condoms; and (B) suction means to draw said condoms through said orienting means.

14. The apparatus of claim 13, further comprising retrieving means to introduce said condoms into said inlet opening.

15. The apparatus of claim 13, further comprising receiving means to receive said condoms from said outlet opening.

16. The apparatus of claim 15, wherein said suction means further draws said condoms to said receiving means.

17. The apparatus of claim 16, wherein said receiving means comprises an apertured nozzle adapted to receive said tip of said condoms and wherein said suction means draws through said apertured nozzle.

18. The apparatus of claim 13, wherein said inner diameter is between one and one and a half inches.

19. The apparatus of claim 13, wherein said inner diameter is approximately one and one quarter inches.

20. The apparatus of claim 13, wherein said orienting tube is between 35 and 100 feet in length.

21. The apparatus of claim 13, wherein said orienting tube is approximately 75 feet in length.

22. The apparatus of claim 13, wherein said retrieving means comprises one or more retrieval tubes, a receptacle to contain said condoms, reciprocating means to reciprocate said retrieval tubes into and out of said receptacle, and retrieval suction means connected to said retrieval tubes to hold said condoms, whereby said reciprocating means positions said condoms held by said retrieval tubes adjacent to said inlet opening of said orienting tube such that said suction means removes said condoms from said retrieval tubes.

23. The apparatus of claim 22, further comprising receptacle moving means for rotating or vibrating said receptacle.

* * * * *